United States Patent [19]
Kita

[11] 4,317,361
[45] Mar. 2, 1982

[54] GAS DENSITY DETECTING DEVICE FOR USE IN INTERNAL COMBUSTION ENGINE

[75] Inventor: Toru Kita, Yokosuka, Japan

[73] Assignee: Nissan Motor Co., Ltd., Tokyo, Japan

[21] Appl. No.: 125,109

[22] Filed: Feb. 27, 1980

[30] Foreign Application Priority Data

Mar. 28, 1979 [JP] Japan ................................ 54-36703

[51] Int. Cl.³ .............................................. G01N 9/26
[52] U.S. Cl. ........................................... 73/30; 73/729
[58] Field of Search .................................... 73/30, 729

[56] References Cited

U.S. PATENT DOCUMENTS

| | | |
|---|---|---|
| 2,399,129 | 4/1946 | Malone . |
| 2,901,718 | 8/1959 | Rehnborg et al. . |
| 3,137,158 | 6/1964 | Krueger ................................. 73/30 |
| 3,357,234 | 12/1967 | Thaler .................................... 73/30 |
| 3,417,607 | 12/1968 | Johnson ................................. 73/30 |
| 4,117,724 | 10/1978 | Cook .................................. 73/729 X |

FOREIGN PATENT DOCUMENTS

| | | |
|---|---|---|
| 2024808 | 10/1971 | Fed. Rep. of Germany ......... 73/30 |
| 1262654 | 2/1972 | United Kingdom . |
| 1266955 | 3/1972 | United Kingdom . |
| 1472543 | 5/1977 | United Kingdom . |

Primary Examiner—Kyle L. Howell
Assistant Examiner—Joseph W. Roskos
Attorney, Agent, or Firm—Lane, Aitken, Kice & Kananen

[57] ABSTRACT

A gas density detecting device for use in an internal combustion engine is disclosed. The device comprises a bellows having a selected gas sealed therein, a guide mechanism provided in the bellows for guiding an expansion motion thereof, a detecting portion provided in the bellows for converting the expansion motion of the bellows into a corresponding electrical output signal, and a correcting resistor provided externally outside of the bellows for correcting the converting factor of the detecting portion.

8 Claims, 3 Drawing Figures

GAS DENSITY DETECTING DEVICE FOR USE IN INTERNAL COMBUSTION ENGINE

BACKGROUND OF THE INVENTION

The present invention relates to a device for detecting gas density for use in an internal combustion engine, and, more particularly, to a gas density detecting device for converting the quantity of air drawn into an engine into a mass flow value.

In automobile engines, when running at high altitudes or under hot climatic conditions, the air density becomes rarefied, so that an air consumption ratio of a fuel mixture is relatively dense as compared with that of the fuel mixture when running at low altitude or under cold climatic conditions and thus a exhaust performance and a fuel consumption efficiency are decreased. The air consumption ratio is therefore usually corrected in accordance with a change in air density, but particularly in the case of an engine equipped with an electronically controlled fuel injecting device, the change of such air density is detected and converted into an electric signal and the electric signal is supplied to a fuel control circuit as a correction signal to adjust the quantity of injected fuel.

A device for detecting air density has been variously proposed as disclosed in Japanese Utility Model Laid-Open No. 4,880/79, for example, the density is often detected by the use of a bellows in which a predetermined gas is sealed based on Boyle-Charles' Law.

This device is comparatively inexpensive, but if the bellows portion is subject to chafing, a measurement error can be generated, and the possibility of a variation in device characteristics at the time of production is comparatively large, so that the use of this type of device is limited.

Moreover, gas density detection is easily influenced by external factors other than a gas according to the measuring condition of the gas to be measured, so that it is difficult to precisely detect gas density.

SUMMARY OF THE INVENTION

It is an object of the present invention to eliminate the above described disadvantages of the conventional gas density detecting device.

It is another object of the present invention to provide a gas density detecting device of high precision and capable of obtaining a control signal by converting the change of gas density into an electrical signal.

According to the present invention a device for detecting gas density comprises a bellows having a selected gas sealed therein, a guide mechanism provided in the bellows for guiding an expansion motion thereof, a detecting portion provided in the bellows for converting the expansion motion of the bellows into an electrical output signal, and a correcting resistor provided at the outside of the bellows for correcting the converting factor of the detecting portion.

The bellows is made of a metal film and is connected to a supporting plate and the gas sealed therein is an inert gas.

The guide mechanism comprises a disc having a rod member, and a cylindrical member having an axial bore therein, the rod member being slidably received in the axial bore of the cylindrical member.

The rod member, the disc, the cylindrical member and the supporting plate are made of a metal or a conductive thermal insulating material.

The detecting portion consists of a slide resistor provided on and along the cylindrical member through a longitudinal insulating plate and a sliding terminal provided on the disc, the sliding terminal slidably contacting the slide resistor in accordance with the expansion movement of the bellows.

A fixed end of the bellows is covered by a thermal insulating casing.

The thermal insulating casing comprises a protecting cover which has venting holes and surrounds a free end of the bellows.

DESCRIPTION OF THE PREFERRED EMBODIMENT

Figure 1:
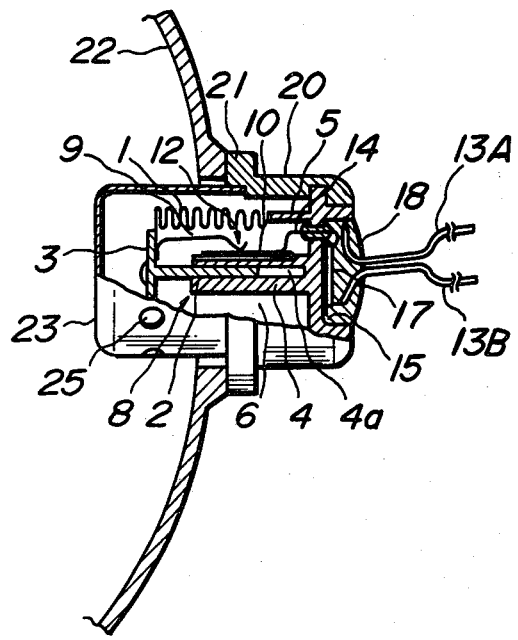
FIG. 1 is a cross-sectional view showing one embodiment of a gas density detecting device according to the present invention.

In FIG. 1 the reference numeral 1 is a bellows fabricated from a metal film having flexible elastic properties such as phosphor bronze. The bellows 1 has a free end sealed in an airtight manner from a disc 3 to which a rod 2 extends at its center, and a fixed end sealed in an airtight manner to a supporting plate 5 from which a cylindrical member 4 extends toward the free end of the bellows 1, thereby defining a hermetic pressure sensing chamber 6 inside the bellows 1 enclosing an inert gas therein.

The disc 3 and the supporting plate 5 are made of a metal or a thermal insulating material, preferably, a conductive thermal insulating material. The rod 2 is slidably received in an axial bore 4a formed in the cylindrical member 4 to define a guide mechanism 8 which ensures smooth, guided expansion and prevents chafing of the bellows 1.

The disc 3 is provided with a sliding terminal 9 fabricated from a material having good conductivity and resilience, such as phosphor bronze. The sliding terminal 9 has a fixed end secured to the disc 3 and a free end slidably contacting a resistor 10 (FIG. 2) provided along the upper side surface of the cylindrical member 4.

Figure 2:
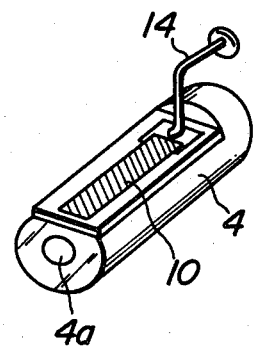
FIG. 2 is a perspective view showing a detecting portion for use in the device according to the present invention.

As shown in FIG. 2, the resistor 10 extends along the cylindrical member 4 in the axial direction, and is defined by a thick film resistor stripe adhered to, for example, an alumina base plate, and is electrically insulated from the cylindrical member 4.

The sliding terminal 9 and the resistor 10 constitute a detecting portion 12 for electrically measuring the displacement of the bellows 1.

A lead wire 13A is connected to a portion of the supporting plate 5 so that an electrical path is formed from the lead wire 13A to the sliding terminal 9 through the supporting plate 5, the bellows 1, and the disc 3. Therefore, the supporting plate 5 and the disc 3 are commonly made of a conductive material, but, for conditions of actual use, a thermal insulating material is preferred in order to avoid measurement errors caused by the transmission of heat from the base portion of the cylindrical member. In the case where a thermal insulating material is used, the supporting plate 5 and the disc 3 are provided with a conductive path, for example, printed wiring or the like.

Figure 3:
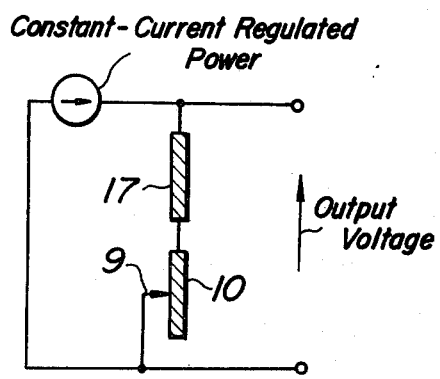
FIG. 3 is a circuit diagram showing a connection arrangement of a resistor plate and a correcting resistor for use in the detecting portion.

The resistor plate 10 is connected to a lead wire 14 at its one end and this wire 14 that extends, in an airtight and insulated manner, through the supporting plate 5 and is connected to one end of a correcting resistor 17 (FIG. 3). The resistor 17 is placed in a recess 15 which is provided at the rear of the supporting plate 5. A lead wire 13B is connected to the other end of the correcting resistor 17 so that the resistors 10 and 17 form an electrical circuit as shown in FIG. 3.

Therefore, if a constant current flows through this circuit the voltage across the resistors 10, 17 changes according to the expansion of the bellows 1.

The correcting resistor 17 is mounted on, but insulated from, the supporting plate 5 and is fabricated from a a thick film resistor. The resistor 17 serves to correct for a slight fluctuation of the bellows displacement resistor value characteristic due to a displacement from an initial position of the sliding terminal 9 and the resistor plate 10 after assembly of the bellows and due to variations in the gas sealing conditions. For example, the detecting portion, after assembly, is placed under the standard temperature and atmosphere pressure, and the correcting resistor 17 is adjusted by trimming to make the combined resistance value of the resistors 10 and 17 constant under the standard conditions, that is, by corresponding to the potential difference between the lead wires 13A and 13B with a desired value, thereby permitting precise correction for the variation in initial positioning during assembly of the bellows.

After correction of the resistance value of the resistor 17, a sealing member 18 consisting of an insulating material such as synthetic resin is deposited in the rear recess 15 to protect the lead wires 13A and 13B and the resistor 17.

Alternatively, the correcting resistor 17 can be provided at the input side of an amplifying circuit.

The supporting plate 5 of the bellows 1 is covered at the outer periphery by a cylindrical casing 20 of a high adiabatic property in order to avoid an error caused by heat transmitted from the device securing portion. The casing 20 is fixed or secured by means of a flange portion 21 to a conduit 22 through which a gas to be measured flows.

The positioning relationship between the flange portion 21 and the casing 20 is determined in such a manner that the bellows 1 projects into the interior of the conduit 22 by one half length of the bellows in the longitudinal direction. The projecting portion of the bellows 1 is covered with a protecting cover 23 which extends beyond the disc 3 by a selected distance.

The protecting cover 23 is provided with a plurality of venting holes 25 so that the gas flows into the cover 23 and directly contacts the outer surface of the bellows 1. The end of the cover 23 is secured to the end portion of the casing 20 so that the cover 23 does not contact the bellows.

In the device according to the present invention constructed above, when the pressure of gas to be measured is changed the bellows 1 enclosing the sealed inert gas therein is expanded according to the change of the pressure thereby changing the contact position of the sliding terminal 9 secured to the free end of the bellows to the resistor plate 10.

Therefore, the resistance value of a circuit formed between the lead wires 13A and 13B is changed in proportion to the expansion of the bellows 1. In this embodiment, the bellows 1 is expanded according to the lowering of the gas pressure thereby to increase the combined resistance value so that the detected output value of gas density is increased according to the lowering of gas pressure to be measured by a constant current flow through the resistors 10 and 17.

When the temperature of the gas to be measured is increased, the temperature of the inert gas enclosed in the bellows 1 is increased resulting in an expansion of the gas until the temperature of the inert gas coincides with the temperature of the gas being measured so that the detected output value of the gas being measured is increased by the expansion of the bellows 1 in response to the the gas expansion.

Therefore, if the pressure and the temperature of the gas to be measured are changed, the density thereof also changes according to the changes of the pressure and the temperature. For example, if the pressure is decreased and the temperature is increased the density decreases so that the present invention can provide an output characteristic for increasing the output value in accordance with the decrease in density.

The expansion motion of the bellows 1 is guided by the guide mechanism 8, so that even if chafing is present or other external forces are present, the expansion motion is always smoothly carried out, and at the same time, the contact of the sliding terminal 9 is always maintained in good condition so that the possibility of a a measurement error is minimized.

Moreover, the bellows 1 is indirectly brought into contact with the conduit 22 for flowing gas to be measured through the thermal insulating casing 20, so that even if the device according to the present invention is secured to an intake manihold of the internal combustion engine, there is no possibility of raising the temperature of the gas sealed in the bellows 1 by engine heat transmitted through the manihold as compared with the gas to be measured, and, as a result, the temperature of the gas flow around the bellows 1 through the venting holes 25 can precisely be sensed and a precise density detecting ability can be obtained.

The detecting portion 12 for electrically detecting the displacement of the bellows 1 is arranged in the pressure sensing chamber 6 enclosing the sealed inert gas (for example, nitrogen gas, helium gas, or the like) therein, so that there is no oxidation, corrosion, or adhesion of contamination at the sliding portion or the like, and a constantly stable function can be exhibited.

As explained above, the present invention can very precisely and electrically detect the density change of the gas to be measured even under the worse measuring condition, and can maintain a stable measuring efficiency for a long time.

Moreover, the present invention can easily correct for quality and manufacturing variation of its characteristic that can occur in the process of production, so that the present invention is well suited to mass-production.

Accordingly, the present invention is suitable in case of carrying out the density measurement of the induced air and correcting the air consumption ratio in the internal combustion engine for automobiles.

What is claimed is:

1. A device for detecting gas density, comprising:
a bellows having a selected gas sealed therein, a guide mechanism provided within the bellows for guiding an expansion motion thereof, a detecting means provided within the bellows for converting the expansion motion of the bellows into an electrical output signal, and a correcting resistor provided exteriorly of the bellows for correcting the electrical signal provided by the detecting means.

2. A device for detecting gas density as claimed in claim 1, wherein the bellows is fabricated from a metal film and connected to a supporting plate and the gas sealed therein is an inert gas.

3. A device for detecting gas density as claimed in claim 1, wherein the guide mechanism comprises a disc having a rod member connected thereto and extending therefrom, and a cylindrical member having an axial bore therein, the rod member being slidably received within the axial bore of the cylindrical member.

4. A device for detecting gas density as claimed in claim 3, wherein the rod member, the disc, the cylindrical member, and the supporting plate are fabricated from a material selected from the group consisting of a metal or a conductive thermal insulating material.

5. A device for detecting gas density as claimed in claim 3, wherein the detecting means comprises a slide resistor mounted on and along the cylindrical member through a longitudinal insulating plate, and a sliding terminal secured to the disc, the sliding terminal in sliding contact with the slide resistor, the contact position between the sliding contact and the slide resistor changing in accordance with the expansion movement of the bellows.

6. A device for detecting gas density as claimed in claim 1, wherein a fixed end of the bellows is covered by a thermal insulating casing.

7. A device for detecting gas density as claimed in claim 6, wherein the thermal insulating casing comprises a protecting cover which surrounds a free end of the bellows and has venting holes formed therein.

8. A device for detecting gas density as claimed in claim 1, wherein the detecting means comprises:
an elongated resistor element mounted on a support means connected to one end of the bellows and a contact terminal connected to the other end of the bellows and in sliding contact with the resistor element whereby expansion and retraction of the bellows causes the position of contact between the contact terminal and the resistor element to vary in response thereto.

* * * * *